United States Patent [19]

Takano et al.

[11] Patent Number: 5,424,462
[45] Date of Patent: Jun. 13, 1995

[54] METHOD FOR PRODUCING (+)-ESTRONE DERIVATIVES

[75] Inventors: Seiichi Takano; Kunio Ogasawara, both of Sendai, Japan

[73] Assignee: Chisso Corporation, Osaka, Japan

[21] Appl. No.: 274,735

[22] Filed: Jul. 18, 1994

Related U.S. Application Data

[62] Division of Ser. No. 177,061, Jan. 3, 1994, abandoned, which is a division of Ser. No. 981,497, Nov. 25, 1992, Pat. No. 5,300,664.

[30] Foreign Application Priority Data

Nov. 25, 1991 [JP] Japan .................................. 3-334554

[51] Int. Cl.6 .............................................. C07J 1/00
[52] U.S. Cl. ................................................ 552/630
[58] Field of Search ......................................... 552/630

[56] References Cited

U.S. PATENT DOCUMENTS 3,451,892  6/1969  Herzog et al. .

FOREIGN PATENT DOCUMENTS 0311033  1/1991  Japan .
980594   1/1965  United Kingdom ................ 552/630

OTHER PUBLICATIONS

CA 85(7): 46943t 1976.
Takano et al, *Concise Enantio–and Stereo-controlled Synthesis of (+)-Equilenin using Chiral Cyclopentadienone Synthon*, Journal of the Chemical Society, Chemical Communications, No. 21, pp. 1544–1546, Nov. 1, 1990.
Quinkert et al, *E. Dane's Route to Estrone Revisited*, Tetrahedron Letters, vol. 32, No. 28, pp. 3357–3360, 1991.
Douglas F. Taber et al, "Enantioselective Ring Contruction: Synthesis of (+)-Estrone Methyl Ether," *J. Organ. Chem.*, pp. 28–34 (1987).
Gary Posner et al, "Total Synthesis of Natural Estrone and Estradiol Methyl Ethers in Extremely High Enantiomeric Purity via an Asymmetric Michael Addition to an Unsaturated Sulfoxide," *J. Am. Chem. Soc.*, pp. 1239–1244 (1986).
G. S. R. Subba Rao et al, "Synthesis Based on Cyclohexadienes. V* A New Approach to the Synthesis of hd a–Ring Aromatic Steroids: A Formal Total Synthesis of (+)-Esterone," *Aust. J. Chem.*, pp. 187–203 (1992).
Seiichi Takano et al, "A Concise Stereocontrolled Total Synthesis of (+)-Esterone," *Tetrahedron Letters*, vol. 33, No. 14, pp. 1909–1910 (1992).

Primary Examiner—Howard T. Mars
Assistant Examiner—Rebecca Cook
Attorney, Agent, or Firm—Browdy and Neimark

[57] ABSTRACT

The present invention provides a method for producing (+)-estrone derivatives, characterized in that it comprises starting from a certain cyclopentadiene derivative, reacting the derivative with a certain diene compound by an asymmetric Diels-Alder reaction, and via intermediates obtaining a (+)-estron derivative represented by the following formula:

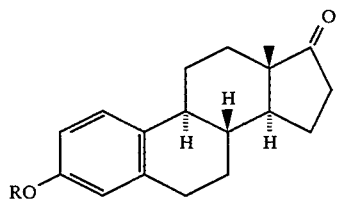

wherein R is alkyl of 1-20 carbon atoms.

According to the present invention, (+)-estron derivatives can be obtained by limited steps from the starting materials of dicyclopentadiene derivatives.

1 Claim, No Drawings

METHOD FOR PRODUCING (+)-ESTRONE DERIVATIVES

This is a division of parent application Ser. No. 08/177,061, filed Jan 3, 1994, now abandoned, itself a division of its parent application Ser. No. 07/981,497, filed Nov. 25, 1992, now U.S. Pat. No. 5,300,664.

BACKGROUND OF THE INVENTION

1. Field of the Invention

The present invention relates to a method for producing (+)-estrone derivatives useful for oral contraceptives by using dicyclopentadiene derivatives as starting materials, and to intermediates which is used for the production of (+)-estrone derivatives.

2. Description of the Prior Art (+)-Estrone is a compound useful for oral contraceptives, and it has been known from a long time to obtain the compound by methods in which natural materials are used (U.S. Pat. Nos. 1967350 (1934) and 135992 (1962). However, the efficiency and yields of the methods are too inferior to those of synthetic methods to compare with.

Synthetic methods of (+)-estrone whose configuration is a natural type have been developed. Posner et al. (J. Am. Chem. Soc., 108) 1239(1986) disclosed that a compound having an AB ring skeleton and a compound having a D ring skeleton which is asymmetrically derived are reacted by an asymmetric Michael addition reaction, and a C ring skeleton is formed by an intramolecular Diels-Alder reaction to construct an estron skeleton having a diastereo selectivity of 91–94%. However, the total yield is low, 6.3%, and the process has inefficiently nine steps.

Moreover, Taber et al. (J. Org. Chem.) 52 $\bar{2}$8(1987)) constructed a β-ketoester having a D ring skeleton by using a camphor derivative as a chiral source, combined the compound with a benzocyclobutene derivative, and constructed a BC ring skeleton by internal cyclization reaction in one step to synthesize (+)-estrone having an optical purity of 91%ee. However, the process has many reaction steps. To construct the β-ketoester, it needs five steps. To synthesize the benzocyclobutene derivative, it needs three steps. To combine the both compounds and to obtain the objective skeleton, it needs three steps. The yield of the ring formation is low, 41%, and the total yield from the β-ketoester precursor is 9.8%. The stereoselectivity of the (+)-estrone is comparatively good, but the efficiency of the process is no good.

Before the present invention, (+)-estrone was much in demand, but it was not provided well.

SUMMARY OF THE INVENTION

As described above, the inventors of the present invention has earnestly studied to attain an object for efficiently obtaining the (+)-estrone derivatives having high optical purities, and they have found that the (+)-estrone is efficiently obtained by using dicyclopentadiene derivative as a starting material.

The present invention is a method for producing (+)-estrone derivatives, characterized in that it comprises starting from (−)-tricyclo [5.2.1.0$^{2,6}$] deca-4,8-diene-3-one (1) represented by the formula:

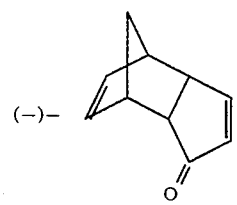

reacting the compound (1) with 4-vinyl-7-alkoxy-1,2-dihydronaphthalene (2) represented by the formula:

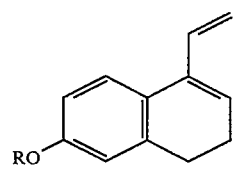

wherein R is alkyl of 1–20 carbon atoms, by employing an asymmetric Diels-Alder reaction, obtaining a compound (3) represented by the formula:

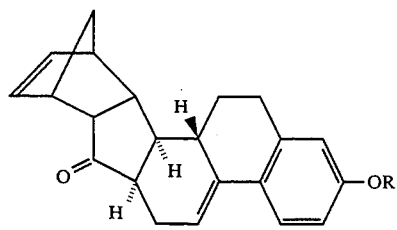

wherein R is the same as described above, and obtaining a (+)-estrone derivative represented by the formula:

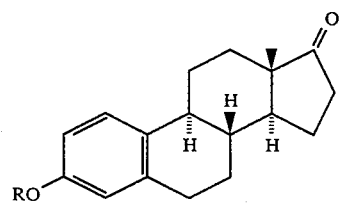

wherein R is the same as described above.

Preferably, in the steps to obtain (+)-estrone derivatives, (4) via compound (3), intermediates are represented by the formulas:

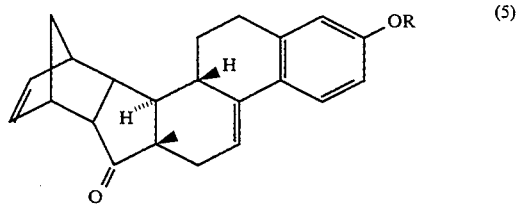

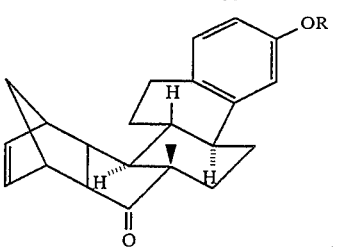

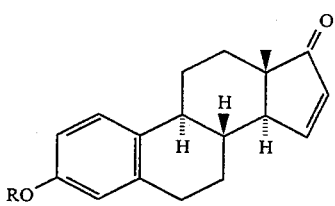

Wherein R is alkyl of 1-20 carbon atoms.

The reaction steps of the production method of the present invention are as follows:

anese Patent Unexamined Publication No. 3-8597(1991)), or acetylating the racemic-tricyclo [5.2.1.0$^{26}$] deca-3-hydroxy-4,6 diene and hydrolyzing the obtained compounds in the presence of lipase by hydrolyzing reaction (J, Chem. Soc, Chem, Commun.) 1989, 271), and obtaining the optically active alcohols.

The obtained (—)-tricyclo [5.2.1.0$^{2.6}$] deca-4,8-diene-3-one (1) and 4-vinyl-7-alkoxy-1,2-dihydronaphthalene (2) which is obtained by a method of Schmidt et al. (Liebigs Ann. Chem., 536, 196 (1938); ibid 537, 246 (1939)) are reacted in the presence of a Lewis acid by an asymmetric Diels-Alder reaction, and the compound (3) can be obtained. As the Lewis acid-used here, diethyl aluminum chloride is preferred, but a compound such as titanium tetrachloride or aluminum chloride, which can catalize the reaction controling the configuration, can be used. The reaction temperature is between —78° C. to —10° C., preferably —30° C.

Hydrocarbons or halogenated solvents can be used as the reaction solvents, especially preferably n-hexane and dichloromethane.

Although the reaction time shall be altered by the treating amounts, usually it is 12-96 hours, preferably 24-36 hours.

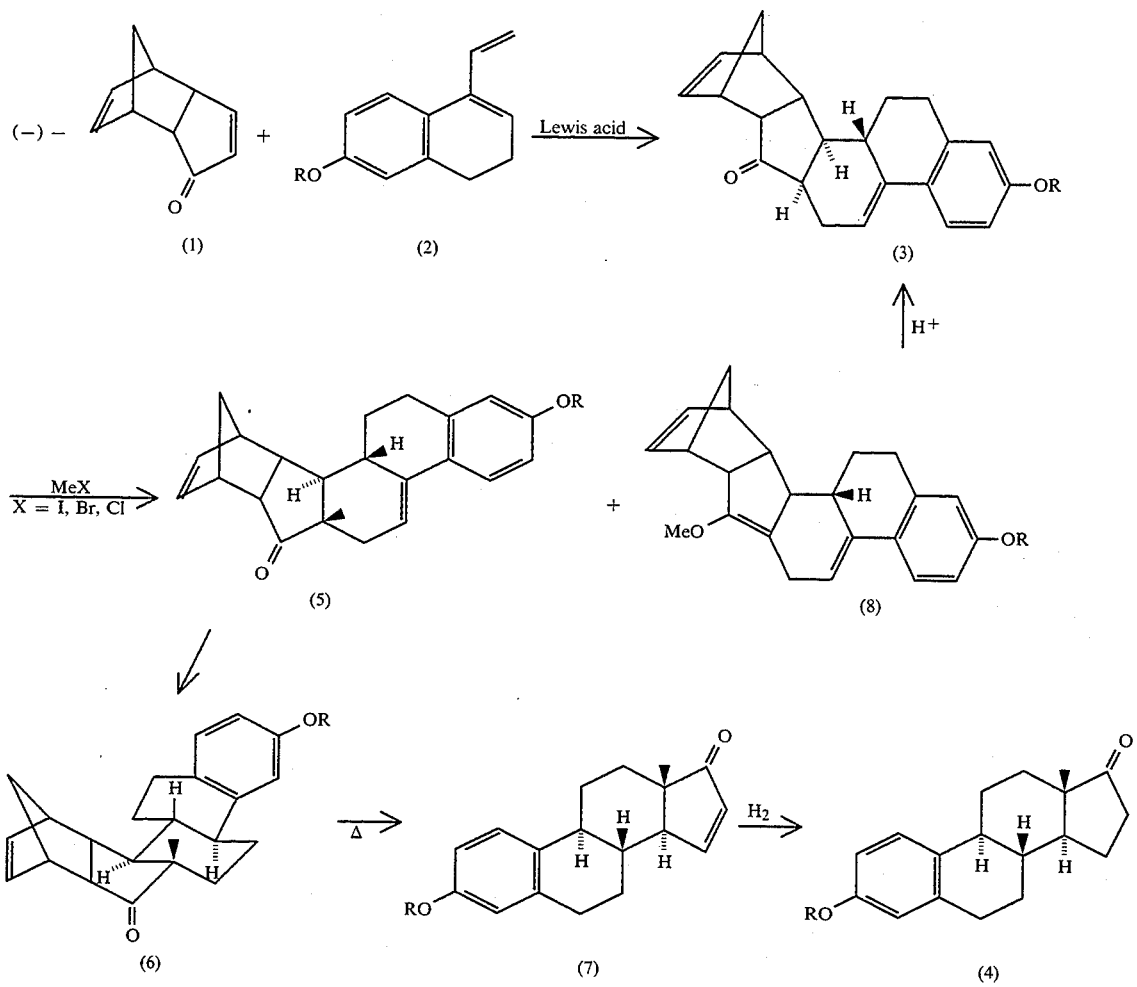

The starting material of the present invention, (—)-tricyclo [5.2.1.0$^{2.6}$] deca-4,8-diene-3-one (1) is obtained by oxidizing dicyclopentadiene with selenium (IV) oxide, reacting the obtained racemic-tricyclo [5.2.1.0$^{2.6}$] deca-3-hydroxy-4,6-diene with an acylating agent in the presence of lipase by a transesterification reaction (Jap- The obtained compound (3) can be converted to the compound (5) by methylation with methyl iodide in the presence of a base. As the base, potassium t-butoxide is preferred. However, any kind of base by which the methylation proceeds can be used. Further, methyl bromide or methyl chloride can be used as a methylation agent.

The compound (8) which is an O-methyl compound obtained as a byproduct in this step is separated off by column chromatography or the like, and the separated compound (8) is treated with hydrochloric acid at 0° C. to easily return to the compound (3), and can be used as a reaction intermediate of (+)-estrone.

The compound (6) is obtained by treating the compound (5) with trifluoroacetic acid and triethyl silane.

Further, by heating the compound (6), the compound (7) is obtained by a retro-Diels-Alder reaction.

At the final step, the compound (7) is reduced at an unsaturated bond by catalytic hydrogenation, and the objective (+)-estrone derivatives (4) can be obtained. A catalyst such as Raney nickel or the like, preferably paradium carbon, can be used.

As described above, (+)-estrone derivatives having high total yield can be obtained by reduced reaction steps from the starting materials of dicyclopentadiene derivatives (1). Considering the recovery of the compound (8), the yield of the (+)-estrone derivatives becomes better.

DESCRIPTION OF THE PREFERRED EMBODIMENTS

The following examples illustrate the present invention more specifically. However, the present invention is not limited by these examples.

EXAMPLE 1

To 25 ml of dichloromethane, 1.72 g (11.8 mmol) of (−)-tricyclo [5.2.1.0$^{2.6}$] deca-4,8-diene-3-one (1) and 2.63 g (14.1 mmol) of 4-vinyl-7-methoxy-1,2-dihydronaphthalene (2) are dissolved, and the mixture was cooled to −30° C. To the solution,. 15 ml (14.1 mmol) of diethyl aluminium chloride (0.94 M, n-hexane solution) was dropwisely added. After being stirred for 32 hours at −30° C., 5% hydrochloric acid was added, and the mixture was extracted with dichloromethane. Then, the dichloromenthane layer was succesively, washed saturated sodium bicarbonate solution and saturated sodium chloride solution, and dried over magnesium sulfate. After dichloromethane was distilled off, the residue was subjected to silica gel column chromatography, and 3.1 g (yield 81.5%) of the compound (3) was obtained.

The physical properties of the compound are as follows:

$[\alpha]_D^{31}$ −168.3° (c 1.01, CHCl$_3$).
IR (film) $\nu_{max}$1730, 1605 cm$^{-1}$.
$^1$H-HMR (500 MHz, CDCl$_3$) J, 1.35 (1H, d, J=8.5 Hz), 1.51 (1H, d, J=7.9 Hz), 1.84 (1H, ddd, J=17.1, 12.2, 4.9 Hz), 1.95–2.02 (1H, m), 2.16–2.27 (2H, m), 2.36–2.51 (3H, m), 2.58–2.62 (1H, m), 2.72–2.91 (4H, m), 3.09–3.12 (1H, m), 3.80 (3H, s), 6.15–6.22 (3H, m), 6.66 (1H, d, J=8.6 Hz), 7.47 (1H, d, J=8.6 Hz).
MS m/z 332 (M+), 266 (100%).
Elemental analysis:
Calculated for C$_{23}$H$_{24}$O$_2$: C 83.10, H 7.28.
Found: C 83.16, H 7.34.

EXAMPLE 2

To a solution of 560 mg (1.96 mmol) of the compound (3) in 8 ml of dimethoxyethane, 37.8 mg (3.37 mmol) of potassium t-butoxide was dropwisely added at room temperature, and the mixture was stirred for 12 minutes. 1.1 ml (17 retool) of methyl iodide was added under cooling with ice, followed by stirring for 12 minutes, adding saturated sodium bicarbonate solution, and extractubg the mixture with ether. The organic layer was washed with saturated sodium chloride solution and dried over magnesium sulfate, the solvent was distilled off, and the residue was subjected to silica gel column chromatography using an eluent of ether/n-hexane (1/1). 334 mg (yield 57%) of the compound (5) and 123 mg (yield 21%) of the compound (8) were obtained from corresponding fractions. The compound (5) was recrystalized from methanol to obtain colorless needle crystals.

The physical properties of the compound are as follows:

$[\alpha]_D^{31}$ +130° (c 0.665, CHCl$_3$).
IR (film) $\nu_{max}$1735, 1606 cm$^{-1}$.
$^1$H-HMR (90 MHz, CDCl$_3$) J, 1.09 (3H, s,), 1.48–2.65 (9H, m), 2.80–3.21 (5H, m), 3.78 (3H, s), 5.81–6.06 (2H, m), 6.10–6.28 (1H, m), 6.57–6.79 (2H, m), 7.39 (1H, d, J=8.3 Hz).
MS m/z 246 (M+ 100%).
Elemental analysis:
Calculated for C$_{24}$H$_{26}$O$_2$: C 83.20, H 7.56.
Found: C 83.21, H 7.78.

EXAMPLE 3

To a solution of 304 mg (0,878 retool) of the compound (5) in 6 ml of dichloromethane, 0.68 ml (8.83 mmol) of trifluoroacetic acid and 0.70 ml (4.38 mmol) of triethyl silane were dropwisely added, and the mixture was stirred for 20 hours at room temperature, followed by adding saturated sodium carbonate under cooling with ice, and extracting the mixture with dichloromethane. The extract was washed with saturated sodium chloride and dried over magnesium sulfate. The solvent was distilled off under reduced pressure, the residue was subjected to silica gel column chromatography using an eluent of ether/n-hexane (1/15), and 2.65 mg (yield 87%) of the compound (6) was obtained from the fraction. The product was recrystalized from methanol to obtain colorless needle crystals.

The physical properties are as follows.
Melting point: 173°–174° C.
$[\alpha]_D^{31}$ +126° (c 0.96, CHCl$_3$).
IR (nujol) $\nu_{max}$1728 cm$^{-1}$.
$^1$H-HMR (500 MHz, CDCl$_3$) J, 1.07 (3H, s,), 1.35–1.48 (3H, m), 1.52–1.74 (5H, m), 2.07–2.18 (2H, m), 2.25–2.32 (1H, m), 2.77 (1H, tb, J=10.4, 4.3 Hz), 2.87–2.98 (3H, m), 3.08 (1H, br, s), 3.24 (1H, dd, J=10.3, 4.2 Hz), 3.77 (3H, s), 6.02 (1H, dd, J=5.5, 3.0 Hz), 6.22 (1H, dd, J=5.5, 3.0 Hz), 6.64 (1H, d, J=3.0 Hz), 6.70 (1H, dd, J=11.0, 2.5 Hz), 7.16 (1H, d, J=9.1 Hz).
MS m/z 348 (M+), 282 (100%).
Elemental analysis:
Calculated for C$_{24}$H$_{28}$O$_2$: C 82.72, H 8.10
Found: C 82.55, H 8.10.

EXAMPLE 4

13 mg (0,037 mmol) of the compound (6) and 1 ml of diphenyl ether were heated and refluxed for 1.5 hours. The reaction solution was subjected to silica gel column chromatography, and 8 mg (yield 76%) of the enone compound (7) was obtained. 4 mg of 10% paradium carbon was added to ethanol solution of 39 mg (0.14 mmol) of the enone compound, and the mixture was stirred for 50 minutes in a stream of hydrogen. After filtering with cerite, the filtrate was concentrated under reduced pressure. The residue was subjected to silica gel column chromatography using an eluent of ether/n-hexane (1/6), and 33 mg (yield 84%) of estrone methyl ether (4) was obtained from the fraction.

The physical properties of the compound are as follows.

Melting point: 174°–175.5° C.
$[\alpha]_D^{33} +159°$ (c 0.72, CHCl$_3$).
IR (nujol) $\nu_{max}$1735 cm$^{-1}$.
$^1$H-HMR (90 MHz, CDCl$_3$) J, 0.88 (3H, s), 1.20–2.51 (13H, m), 2.72–2.98 (2H, m), 3.77 (3H, s), 6.54–6.67 (2H, m), 6.55–6.76 (1H, m), 7.20 (1H, d, J=8.3 Hz).
MS m/z 248 (M+ 100%).

EXAMPLE 5

To 5 ml of a mixture solvent of 10% HCl-THF (1:3) having a temperature of 0° C., 123 mg of the compound (8) (melting point 103°–105° C., $[\alpha]_D^{33}+215°$ (c 1.0.1, CHCl$_3$) was dissolved. Upon slowly warming from 0° C. to room temperature, the mixture was stirred for 1.5 hours. Saturated sodium bicarbonate was added to the mixture under cooling with ice, the neutralized mixture was extracted with dichloromethane, and the extract layer was washed with sodium chloride and dried over magnesium sulfate. After dichloromethane was distilled off, the residue was subjected to silica gel column chromatography, and 1 00 mg of the compound (3) was quantitatively obtained.

We claim:

1. A method for producing a (+)-estrone derivative represented by the formula:

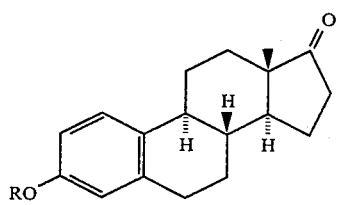

(4)

comprising the steps of:
reacting (—)-tricyclo [5.2.1.0$^{2.6}$] deca-4,8-diene-3-one (1) represented by the formula:

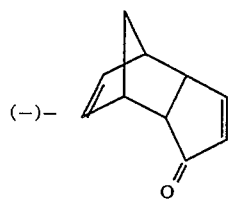

(1)

with 4-vinyl-7-alkoxy-1,2-dihydronaphthalene (2) represented by the formula:

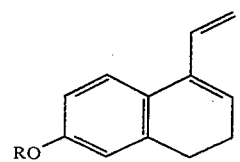

(2)

wherein R is alkyl of 1–20 carbon atoms, in the presence of a Lewis acid to obtain a compound (3) represented by the formula:

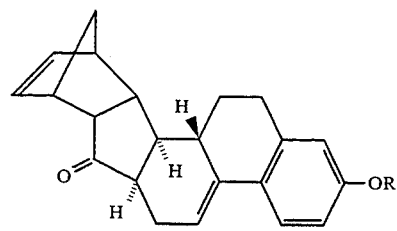

(3)

wherein R is the same as described above; reacting said compound (3) with a methyl halide in the presence of a base to obtain a compound (5) represented by the formula:

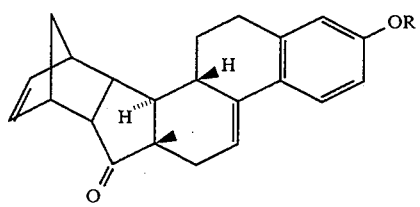

(5)

wherein R is the same as described above;
treating said compound (5) with trifluoroacetic acid and triethylsilane to obtain a compound (6) represented by the formula:

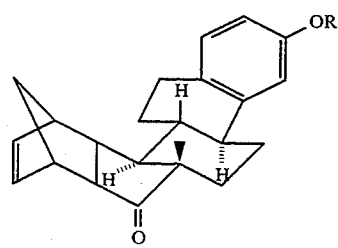

(6)

wherein R is the same as described above;
heating said compound (6) to obtain a compound (7) represented by the formula:

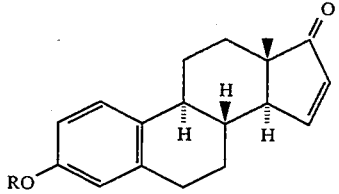

(7)

by a retro-Diels-Alder reaction;
and reducing said compound (7) by catalytic hydrogenation to obtain said (+)-estrone derivative (4).

* * * * *